United States Patent [19]

Holtkamp, Sr.

[11] Patent Number: Plant 7,323

[45] Date of Patent: Sep. 11, 1990

[54] AFRICAN VIOLET PLANT NAMED LITTLE MOONSTONE

[76] Inventor: Reinhold Holtkamp, Sr., Blumenstrasse 28, D 4242 Rees-Haffen, Fed. Rep. of Germany

[21] Appl. No.: 363,465

[22] Filed: Jun. 8, 1989

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Little Moonstone characterized by its miniature growth habit; double white flowers with light blue touch in the center, strong stems which curve toward the center to form a compact bouquet above the leaves; profuse and continuous flowering; bright green, serrated, round leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Moonstone.

The new cultivar was referred to during the breeding and selection process by the designation W 19/W and is a product of a planned breeding program. The new cultivar was originated from a cross made by me in the controled breeding program in Haffen, Federal Republic of Germany. The female, or seed parent was a cultivar designated 24. The male, or pollen parent was a cultivar designated H 25/z.

Little Moonstone was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Moonstone has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn. under greenhouse conditions which closely approximate those generally used in commercial practice.

The following traits have been repeatedly observed and are determined to be basic characteristics of Little Moonstone, which in combination distinguish this African violet as a new and distinct cultivar:

(1) Little Moonstone will not grow taller than 8 cm.

(2) Double white flowers with light blue touch in the center.

(3) Strong wirelike and upright flower stems curving toward the center.

(4) First flash of flowers form a tight bouquet above the leaves.

(5) Profuse flowering; under good growing conditions continuous flowering.

(6) Each plant carries 7–8 and more upright flower stems each of which carries 5–7 and more flowers.

(7) Long lasting, non-dropping flowers.

(8) Plant saleable 10 to 11 weeks after planting of unrooted shoot.

(9) Seed capsules push slightly through.

(10) Bright green, hairy leaves.

(11) Round leaves are serrated and approximately 3 cm in size.

(12) After maturity the flowers dry off, and remain on the peduncle.

The accompanying color photographic drawing shows a typical specimen plant of the new cultivar grown in a 4 cm pot. The plant is pictured next to a ruler, highlighting the miniature size and growth habit of Little Moonstone. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 1 p.m. in Nashville, Tenn.

Botanical classification: *Saintpaulia ionantha,* Ramat., c.v. Little Moonstone.

Parentage:

*Male parent.*—H 25/z.

*Female parent.*—24.

Propagation: The new cultivar holds its distinguishing characteristics through successive propagations by leaf cuttings.

Plant: From 5 cm to 7 cm tall when grown in pots, and approximately 9–10 cm in diameter when fully grown.

*Leaves.*—General form: Round. Diameter: approximately 30 mm. Texture: Velvety. Aspect: Serrated, shiny, hairy. Veins: Upperside: visible; underside: well pronounced, light green, shiny. Color (upperside): Yellow-Green Group 147 A. Color (underside): Yellow-Green Group 148 D. Petiole: Strong, green, hairy.

*Flowers.*—Buds: Size: 3–4 mm just before opening. Shape: Bell-shaped. Color: Greenish white. Sepals: Five (5). Color: Green. Calyx: Shape: Funnel-shaped. Aspect: Spear-shaped, hairy. Peduncle: Character: Strong upright, hairy. Color: Green. Individual flowers: Size: 22–25 mm.

Shape: Double, round-looking. Color (upperside): White with center being Violet-Blue Group 93 C to D in the center. Under cooler temperatures and more intensive lighting, the bluish color in the center tends to intensify. Color (underside): White with occasional touch of Violet-Blue Group 93 D. Borne: Each flower stem carries 5–7 and more flowers on strong, upright peduncle that are free standing above the leaves, thereby forming a compact bouquet. Flowering habit: Flowers 10–11 weeks after planting an unrooted plantlet.

Reproductive organs:

*Stamens.*—Two (2). Anthers: 2 composed of 4 anther cells, seed capsule pushes slightly through.

*Filaments.*—Yellowish green, 3–4 mm long.

*Styles.*—4–5 mm long, purplish, base of ovary light green and hairy.

Roots: Normally developed, white when young, turning slightly brownish when older.

Disease resistance: Good.

General observations: Little Moonstone is a super miniature violet, which does not grow taller than 8 cm.

The double flowers are white with a touch of light blue in the center. They have up to 20 petals of varying size and are round-looking. The anthers are covered up. The flowers are long-lasting and non-dropping. Under good growing conditions, Little Moonstone will bloom continuously. A nice bouquet of flowers free standing above the bright green, round leaves develops approximately 10–11 weeks after planting an unrooted plantlet. Each of the 7–8 and more strong stems carries 5–7 and more flowers.

I claim:

1. A new and distinct cultivar of African violet named Little Moonstone, as described and illustrated, and particularly characterized by its miniature growth habit; double white flowers with light blue touch in the center, strong stems which curve toward the center to form a compact bouquet above the leaves; profuse and continuous flowering; bright green, serrated, round leaves; flowering 10–11 weeks after planting of unrooted shoot, and by its long lasting and non-dropping flowers.

* * * * *

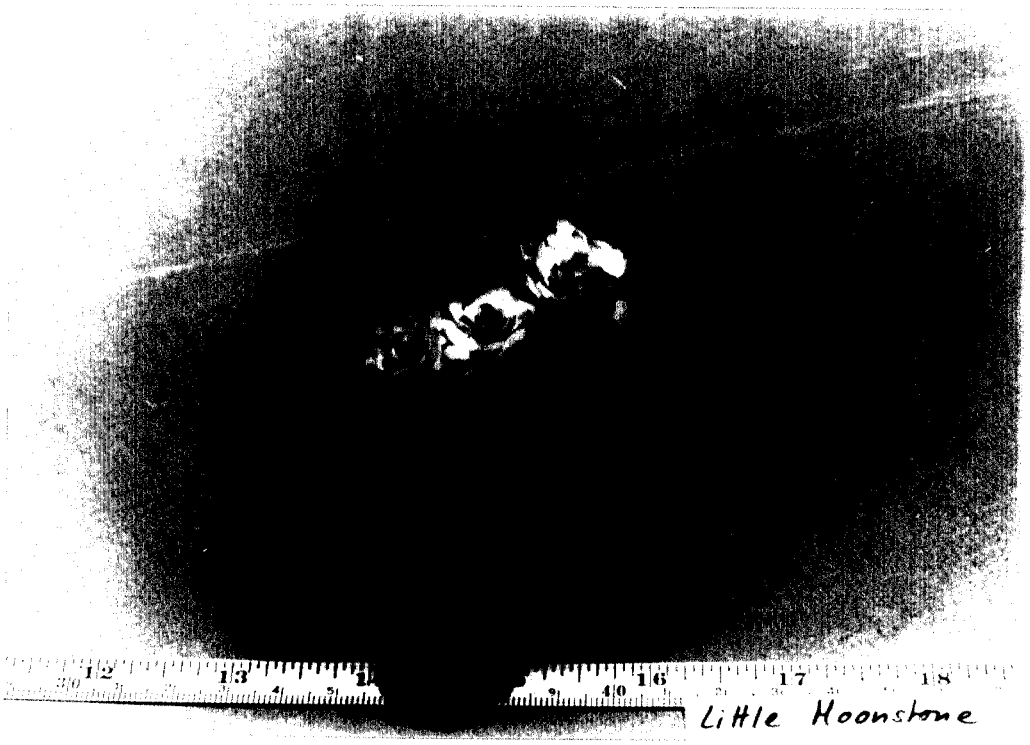
Little Moonstone